US011278635B2

(12) United States Patent
Durance et al.

(10) Patent No.: US 11,278,635 B2
(45) Date of Patent: Mar. 22, 2022

(54) METHOD AND APPARATUS FOR PASTEURIZING AND DEHYDRATING CANNABIS

(71) Applicant: Enwave Corporation, Delta (CA)

(72) Inventors: Timothy D. Durance, Vancouver (CA); Gary Sandberg, Chilliwack (CA); Jun Fu, Port Coquitlam (CA); Guopeng Zhang, Surrey (CA)

(73) Assignee: ENWAVE CORPORATION, British Columbia (CA)

( * ) Notice: Subject to any disclaimer, the term of this patent is extended or adjusted under 35 U.S.C. 154(b) by 92 days.

(21) Appl. No.: 16/641,885

(22) PCT Filed: Aug. 30, 2017

(86) PCT No.: PCT/CA2017/051025
§ 371 (c)(1),
(2) Date: Feb. 25, 2020

(87) PCT Pub. No.: WO2019/041017
PCT Pub. Date: Mar. 7, 2019

(65) Prior Publication Data
US 2020/0246495 A1    Aug. 6, 2020

(51) Int. Cl.
| A61L 2/12 | (2006.01) |
| A61L 2/00 | (2006.01) |
| A61L 2/26 | (2006.01) |
| F26B 5/04 | (2006.01) |
| F26B 17/04 | (2006.01) |

(Continued)

(52) U.S. Cl.
CPC ............... *A61L 2/0064* (2013.01); *A61L 2/12* (2013.01); *A61L 2/26* (2013.01); *F26B 5/048* (2013.01);

(Continued)

(58) Field of Classification Search
CPC . A61L 2/0064; A61L 2/12; A61L 2/26; A61L 2202/11; A61L 2202/122;

(Continued)

(56) References Cited

U.S. PATENT DOCUMENTS

| 4,896,005 A | 1/1990 | Skubich |
| 5,972,397 A | 10/1999 | Durance et al. |
| 6,381,873 B1 | 5/2002 | Peremychtchev et al. |
| 7,007,405 B2 * | 3/2006 | Hajek ..................... F26B 3/347 34/259 |
| 8,286,366 B2 | 10/2012 | Pittari et al. |

(Continued)

FOREIGN PATENT DOCUMENTS

| CA | 2184384 | 7/1996 |
| EP | 2525675 | 7/2011 |

(Continued)

OTHER PUBLICATIONS

Yaghmaee, Efficacy of Vacuum Microwave Drying in Microbial Decontamination of Dried Vegetables (abstract), Drying Technology, vol. 25, Issue 6 (2007).

*Primary Examiner* — Timothy C Cleveland
(74) *Attorney, Agent, or Firm* — Nyemaster Goode P.C.

(57) ABSTRACT

A method and apparatus for pasteurizing and drying cannabis plant materials using a microwave-vacuum chamber. The pasteurizing and drying are carried out with no use of ionizing radiation and with rapid drying. Pasteurization is done at a temperature and for a time period that are sufficient to reduce microorganisms to an acceptably low level, while not significantly reducing the psychoactive compounds in the material. In the process, the pressure inside a vacuum chamber is reduced to a first pressure less than atmospheric. The material is maintained in the vacuum chamber at the first pressure at a pasteurizing temperature while irradiating the material with microwave radiation. The pressure is then reduced to a second pressure lower than the first pressure and the material is maintained in the vacuum chamber at the second pressure for a time period at a dehydrating temperature lower than the pasteurizing temperature while irradiating the material with microwave radiation. The pasteurizing and dehydrating steps can be done in the reverse order.

19 Claims, 1 Drawing Sheet

(51) Int. Cl.
   *F26B 21/10* (2006.01)
   *F26B 25/00* (2006.01)
(52) U.S. Cl.
   CPC .............. *F26B 17/04* (2013.01); *F26B 21/10* (2013.01); *F26B 25/002* (2013.01); *A61L 2202/11* (2013.01); *A61L 2202/122* (2013.01); *A61L 2202/21* (2013.01)
(58) Field of Classification Search
   CPC ...... A61L 2202/21; F26B 5/041; F26B 5/042; F26B 5/048; F26B 17/04; F26B 21/10; F26B 25/002
   See application file for complete search history.

(56) References Cited

U.S. PATENT DOCUMENTS

| | | |
|---|---|---|
| 2005/0123435 A1 | 6/2005 | Cutler et al. |
| 2008/0083749 A1 | 4/2008 | Kantor et al. |
| 2014/0328867 A1 | 11/2014 | Fu et al. |
| 2015/0096189 A1 | 4/2015 | Hawes et al. |
| 2018/0221522 A1* | 8/2018 | Eades ................. F26B 5/04 |

FOREIGN PATENT DOCUMENTS

| | | |
|---|---|---|
| WO | 2010/013583 | 2/2010 |
| WO | 2014075193 A1 | 5/2014 |
| WO | 2014085897 | 6/2014 |
| WO | 2016044571 | 3/2016 |
| WO | 2018148430 | 8/2018 |

* cited by examiner

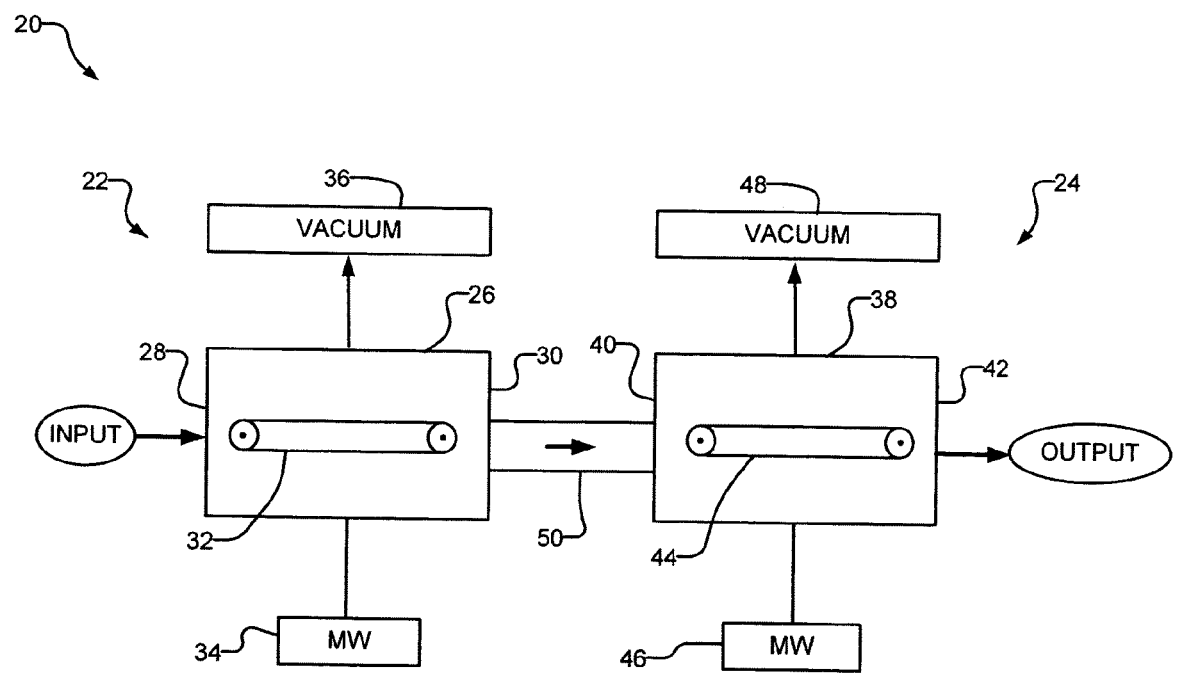

METHOD AND APPARATUS FOR PASTEURIZING AND DEHYDRATING CANNABIS

PRIORITY

This application is a U.S. national stage application under 35 USC § 371 of International Application No. PCT/CA2017/051025, filed Aug. 30, 2017, which is incorporated by reference in its entirety into this application.

FIELD OF THE DISCLOSURE

The present disclosure pertains to the methods and apparatus for the preparation of cannabis for human use.

BACKGROUND OF THE DISCLOSURE

Both pasteurization and dehydration are steps that may be used in preparing plant matter, such as cannabis, for human use, whether medical or, where legal, recreational use. It may be desirable for dehydration to retain sufficient terpenes and/or other cannabinoids, such as THC (tetrahydrocannabinol) or other psychoactive chemical ingredients, depending on the usage regimen for a particular strain of plant matter.

Pasteurization may be used to destroy potentially pathogenic microorganisms that may be present on the cannabis plant material. Because cannabis for human use may be consumed in various ways, pathogenic microorganisms may be carried into the body and cause pneumonia or other disease conditions. Pasteurization may be more important in medical applications because the patients are often immunocompromised and hence especially vulnerable to infections.

The current practice in the industry is to dry the cannabis plant material by air drying at room temperature, which typically requires five to six days. Decontamination is done by means of ionizing radiation, which is the only pasteurization technique currently available to the industry. It is carried out using highly specialized equipment, typically at a facility separate from the drying facility, making it an expensive and troublesome operation for the cannabis industry. It is also a controversial process for some patients and consumers because ionizing radiation is considered an undesirable process by some consumers, especially in some European countries such as Germany. Moreover, the cost of production is increased by the security required at both facilities and during transport between them.

SUMMARY OF THE DISCLOSURE

The present disclosure provides a method of pasteurizing and drying cannabis plant materials in which the pasteurizing and drying processes are carried out in a single facility, even in a single apparatus, with no use of ionizing radiation and with rapid drying, producing a high quality product.

In an aspect of the present disclosure, the pasteurization and dehydration of cannabis plant material can be done using microwave radiation at reduced pressure in a vacuum chamber, in a manner that effectively pasteurizes the plant material, and dries it, while not significantly reducing the active components in the material. The pasteurization is done at a temperature and for a time period that are sufficient to reduce microorganisms to an acceptably low level. High levels of terpenes and other desired chemical components are retained in the dried material.

One aspect of the present disclosure provides a method of pasteurizing and dehydrating cannabis plant material, such as flower buds, leaves and stems, comprising the steps of: (a) loading the cannabis plant material into a vacuum chamber; (b) reducing pressure inside the vacuum chamber to a first pressure less than atmospheric (c) maintaining the cannabis plant material in the vacuum chamber at the first pressure for a first time period at a pasteurizing temperature while irradiating the cannabis plant material with microwave radiation; (d) reducing the pressure in the vacuum chamber after step (c) to a second pressure lower than the first pressure; (e) maintaining the cannabis plant material in the vacuum chamber at the second pressure for a second time period at a dehydrating temperature lower than the pasteurizing temperature while irradiating it with microwave radiation to dehydrate it; and (f) unloading the pasteurized and dehydrated cannabis plant material from the vacuum chamber.

Another aspect of the present disclosure provides a continuous-throughput method of pasteurizing and dehydrating cannabis plant material, comprising the steps of: (a) reducing pressure inside a first vacuum chamber to a first pressure less than atmospheric; (b) loading the cannabis plant material into the first vacuum chamber; (c) maintaining the cannabis plant material in the first vacuum chamber at the first pressure for a first time period at a pasteurizing temperature while irradiating it with microwave radiation; (d) unloading the pasteurized cannabis plant material from the first vacuum chamber; (e) reducing pressure in a second vacuum chamber to a second pressure lower than the first pressure; (f) loading the pasteurized cannabis plant material into the second vacuum chamber; (g) maintaining the pasteurized cannabis plant material in the second vacuum chamber at the second pressure for a second time period at a dehydrating temperature lower than the pasteurizing temperature while irradiating it with microwave radiation to dehydrate it; and (h) unloading the pasteurized and dehydrated cannabis plant material from the second vacuum chamber.

In some embodiments, the step of dehydrating precedes pasteurizing.

An aspect of the present disclosure provides a method of dehydrating and pasteurizing cannabis plant material, comprising the steps of: (a) loading the cannabis plant material into a vacuum chamber; (b) reducing pressure inside the vacuum chamber to a first pressure less than atmospheric; (c) maintaining the plant materials in the vacuum chamber at the first pressure for a first time period at a dehydrating temperature while irradiating it with microwave radiation to dehydrate it; (d) increasing the pressure in the vacuum chamber after step (c) to a second pressure higher than the first pressure; (e) maintaining the cannabis plant material in the vacuum chamber at the second pressure for a second time period at a pasteurizing temperature higher than the dehydrating temperature while irradiating it with microwave radiation; and (f) unloading the dehydrated and pasteurized cannabis plant material from the vacuum chamber.

Yet another aspect of the present disclosure provides a method of dehydrating and pasteurizing cannabis plant material, comprising the steps of: (a) reducing pressure inside a first vacuum chamber to a first pressure less than atmospheric; (b) loading the cannabis plant material into the first vacuum chamber; (c) maintaining the cannabis plant material in the first vacuum chamber at the first pressure for a first time period at a dehydrating temperature while irradiating the cannabis plant material with microwave radiation; (d) unloading the dehydrated cannabis plant material from the first vacuum chamber; (e) reducing pressure in a second vacuum chamber to a second pressure higher than the first pressure; (f) loading the dehydrated cannabis plant material into the second vacuum chamber; (g) maintaining the dehydrated cannabis plant material in the second vacuum chamber at the second pressure for a second time period at a pasteurizing temperature higher than the dehydrating temperature while irradiating the dehydrated cannabis plant material with microwave radiation; and (h) unloading the dehydrated and pasteurized cannabis plant material from the second vacuum chamber.

A further aspect of the present disclosure provides an apparatus for pasteurizing and drying an organic material, such as marijuana plant material, comprising: (a) a first microwave-vacuum unit, comprising: (i) a first vacuum chamber having an input end for introduction of the organic material and an output end for removal of the organic material, (ii) a first conveyor for conveying the organic material from the input end to the output end, (iii) a first microwave source arranged to irradiate microwave energy into the first vacuum chamber, and (iv) a first vacuum source for reducing pressure inside the first vacuum chamber to a first pressure below atmospheric, (b) a second microwave-vacuum unit downstream of the first microwave-vacuum unit, comprising: (i) a second vacuum chamber having an input end for introduction of the organic material and an output end for removal of the organic material, (ii) a second conveyor for conveying the organic material from the input end to the output end, (iii) a second microwave source arranged to irradiate microwave energy into the second vacuum chamber, and (iv) a second vacuum source for reducing pressure inside the second vacuum chamber to a second pressure different from the first pressure; and (c) a conveyor for transferring the organic material from the output end of the first vacuum chamber to the input end of the second vacuum chamber.

Further aspects of the present disclosure and features of specific embodiments of the present disclosure are described below.

BRIEF DESCRIPTION OF THE DRAWING

FIG. 1 is a schematic diagram of a pasteurizing and drying apparatus according to one embodiment of the present disclosure.

DETAILED DESCRIPTION

A process in accordance with an aspect of the present disclosure pasteurizes and dries cannabis plant material using a microwave vacuum chamber. The plant material comprises parts of the plant containing terpenes and other desired components, and may include cannabis flower buds, leaves and stems.

Apparatuses for applying microwave radiation to organic materials in a vacuum chamber are known, and have conventionally been used in the food processing and pharmaceutical industries. They are disclosed, for example, in WO 2009/049409 (Durance et al.), WO 2011/085467 (Fu et al.), WO 2013/010257 (Fu et al.), and WO 2014/085897 (Durance et al.).

In the present disclosure, the cannabis plant material is placed in the vacuum chamber and vacuum is applied to reduce the pressure to below atmospheric. The reduced pressure is selected such that the boiling point of water at that pressure is at a temperature that may be sufficient to pasteurize the cannabis plant material, i.e. reduce microorganism numbers to an acceptably low level, while not being significantly destructive to the terpenes and other desired compounds in the plant material. For example, the THC content may be reduced by not more than 5% and the terpene content by not more than 35%.

In an aspect of the present disclosure, the pasteurization pressure may be in the range of 150 to 400 Torr (200 to 533 mbar), alternatively 180 to 300 Torr (240 to 400 mbar), resulting in a pasteurization temperature in the range of 60 to 95° C., alternatively 62 to 88° C., alternatively 70 to 80° C., alternatively 65 to 80° C. "Pasteurization temperature" as used in the present disclosure means the temperature of the plant material during the pasteurization step. Microwave radiation is applied to the plant material during the pasteurization step, and during the subsequent drying step, to heat the plant material and evaporate water. The pasteurization step is conducted for a time period in the range of 3 to 12 minutes, alternatively 3 to 10 minutes, alternatively 7 to 10 minutes. The listed pasteurization times and temperatures may be sufficient to produce cannabis plant material that meets microbial regulatory standards, e.g., a total plate count 50,000 colony-forming unit per gram ("cfu/g"), total yeast and mold 500 cfu/g, and bile tolerant gram negative bacteria (BTGN)<100 cfu/g.

Immediately following the pasteurization step, the pressure in the vacuum chamber is reduced from the pasteurization pressure to a pressure corresponding to a drying temperature that is lower than the pasteurization temperature and is sufficient to achieve drying of the plant material within a selected time period. For example, the drying pressure may be in the range of 10 to 60 Torr (13 to 80 mbar), alternatively 25 to 40 Torr (33 to 53 mbar), alternatively 25 to 35 Torr (25 to 47 mbar) Torr. The drying temperature may be in the range of 40 to 60° C. "Drying temperature" means the temperature of the plant material during the drying step. At 40 Torr, the boiling point is 35° C., though the actual product temperature becomes somewhat higher than this due to presence of solutes in the water which are concentrated as water is evaporated off. The drying step is conducted at this reduced pressure and with microwave radiation heating the material, for a time period sufficient to reduce the water content of the material to a desired level. For example, the drying time may be in the range of 20 to 30 minutes, alternatively 22 to 27 minutes, alternatively 15 to 25 minutes, and the final moisture level may be in the range of 8 to 14 wt. %. The term "drying time" as used herein does not include the time period for the pasteurization step.

The cannabis plant material may be moved within the vacuum chamber during the pasteurization and drying steps, for example by means of a rotating basket, a rotating tray rack, trays conveyed through the vacuum chamber, or a conveyor belt. This provides a more even exposure of the plant material to the microwave field within the chamber. The cannabis plant material may optionally be covered by a microwave-transparent perforated cover during the pasteurization step and/or the drying step; this retains steam sufficiently to ensure a uniform cannabis plant material temperature during the pasteurization step but allows steam to escape during the drying step.

In the process as described above, the step of pasteurization is conducted before the step of dehydration. This order is preferred, because the microbial population is more effectively reduced in plant material that is relatively moist. Nevertheless, it is possible carry out the process with the step of dehydration before the step of pasteurization. As shown in Example 2 below, which used this reverse order of the steps, the amount of reduction of Total Plate Count and of final yeast and mold count was less than where the order was pasteurization followed by dehydration, as in Examples 1 and 3 to 6.

According to an embodiment of the process in which dehydration is conducted before pasteurization, the cannabis plant material is loaded into the vacuum chamber and the pressure inside the vacuum chamber is reduced to a first pressure less than atmospheric. The cannabis plant material is maintained in the vacuum chamber at the first pressure for a first time period at a dehydrating temperature while irradiating the cannabis plant material with microwave radiation to dehydrate it. The pressure in the vacuum chamber is then increased to a second pressure higher than the first pressure. The cannabis plant material is maintained in the vacuum chamber at the second pressure for a second time period at a pasteurizing temperature higher than the dehydrating temperature while irradiating the cannabis plant material with microwave radiation. Finally, the dehydrated and pasteurized cannabis plant material is unloaded from the vacuum chamber. The pressures, temperatures and times for the steps of dehydration and pasteurization are the same as described above in respect of the process in which pasteurization is conducted before dehydration.

The processes as described above can be conducted in a single microwave vacuum chamber, with the plant material being loaded into the vacuum chamber through an access port and unloaded at the end of the process, following re-pressurization of the chamber to atmospheric, from the same access port. Such apparatus is suitable for batch processing of the material.

According to another embodiment, the pasteurization and drying process is conducted on a continuous throughput basis rather than a batch basis. FIG. 1 schematically illustrates a pasteurization and drying apparatus 20 that can be used for the continuous-throughput process. The same form of apparatus may be used both for the process in which pasteurization precedes dehydration and the process in which dehydration precedes pasteurization. The apparatus 20 comprises two microwave vacuum units, namely, a first unit 22 and a second, downstream unit 24. The first microwave vacuum unit 22 comprises a first vacuum chamber 26 having an input end 28 for introduction of the material and an output end 30 for removal of the material. A first conveyor 32 conveys the material from the input end to the output end of the first vacuum chamber. A first microwave source 34 is arranged to irradiate microwave energy into the first vacuum chamber. A first vacuum source 36 is operatively connected to the first vacuum chamber for reducing pressure inside it to a first pressure below atmospheric.

The second microwave vacuum unit 24 is arranged downstream of the first microwave vacuum unit. It comprises a second vacuum chamber 38 having an input end 40 for introduction of the material and an output end 42 for removal of the material. A second conveyor 44 conveys the material from the input end to the output end of the second vacuum chamber. A second microwave source 46 is arranged to irradiate microwave energy into the second vacuum chamber. A second vacuum source 48 is operatively connected to the second vacuum chamber for reducing pressure inside it to a second pressure different from the first pressure. The apparatus 20 has a conveyor 50 for transferring the organic material from the output end of the first vacuum chamber to the input end of the second vacuum chamber. The conveyor 50 may be at atmospheric pressure, so that the product is released to the atmosphere after treatment in the first unit 22. Optionally, the conveyor 50 may include a vacuum lock so that the pasteurized product is maintained at reduced pressure between the pasteurization and drying steps. Optionally, the conveyors 32, 44 may include means for rotating or tumbling the plant material. Optionally, the apparatus may include a microwave-transparent perforated cover for covering the plant material. Where the apparatus 20 is used to carry out the process in which pasteurization precedes dehydration, the first unit 22 is the pasteurization unit, and the second, downstream unit 24 is the drying unit. Where the apparatus 20 is used to carry out the process in which dehydration precedes pasteurization, the first unit 22 is the drying unit, and the second, downstream unit 24 is the pasteurization unit.

The apparatus 20 includes components that are conventionally required for microwave-vacuum dehydrators, including condensers, refrigeration units, vacuum pumps, water loads, air locks and a programmable logic controller (PLC) for controlling the operation of the system, including controlling the conveyor drive motors, the microwave generators, the vacuum pumps and the refrigerant pumps.

The continuous-throughput process, in which pasteurization precedes dehydration, is carried out using the apparatus 50 as follows. The pressure inside the first vacuum chamber 26 is reduced to a first pressure less than atmospheric and the cannabis plant material is loaded into the first vacuum chamber. Optionally, the plant material may be covered by a microwave-transparent perforated cover. The cannabis plant material is maintained in the first vacuum chamber 26 at the first pressure for a first time period at a pasteurizing temperature while irradiating the cannabis plant material with microwave radiation as it is moved by the conveyor 32. The pasteurized cannabis plant material is then unloaded from the first vacuum chamber via the conveyor 50. It is fed into the second vacuum chamber 38, having a second pressure lower than the first pressure. The pasteurized cannabis plant material in the second vacuum chamber is maintained at the second pressure for a second time period at a dehydrating temperature lower than the pasteurizing temperature while being moved through the second vacuum chamber and irradiated with microwave radiation to dehydrate it. Finally, the pasteurized and dehydrated cannabis plant material is unloaded from the output end 42 of the second vacuum chamber.

Similarly, the continuous-throughput process in which dehydration precedes pasteurization is carried out using the apparatus 50 as follows. The pressure inside the first vacuum chamber 26 is reduced to a first pressure less than atmospheric and the cannabis plant material, optionally covered, is loaded into the first vacuum chamber. The cannabis plant material is maintained in the first vacuum chamber 26 at the first pressure for a first time period at a drying temperature while irradiating the cannabis plant material with microwave radiation as it is moved by the conveyor 32. The dehydrated cannabis plant material is then unloaded from the first vacuum chamber via the conveyor 50. It is fed into the second vacuum chamber 38, having a second pressure higher than the first pressure. The pasteurized cannabis plant material in the second vacuum chamber is maintained at the second pressure for a second time period at a pasteurizing temperature higher than the drying temperature while being moved through the second vacuum chamber and irradiated with microwave radiation. Finally, the dehydrated and pasteurized cannabis plant material is unloaded from the output end 42 of the second vacuum chamber.

An example of a microwave-vacuum dehydrator that is suitable for use as the pasteurizing unit and as the drying unit is a resonant cavity-type microwave apparatus, as shown in WO 2009/049409 (Durance et al.), commercially available from EnWave Corporation of Vancouver, Canada, under the trademark nutraREV. Using this type of apparatus, the cannabis plant material is placed for treatment in a cylindrical basket that is transparent to microwave radiation and has openings to permit the escape of moisture. The loaded basket is placed in the vacuum chamber with its longitudinal axis oriented horizontally. The pressure in the chamber is reduced. The microwave generator is actuated to radiate microwaves in the vacuum chamber and the basket is rotated within the vacuum chamber, about a horizontal axis, so as to slowly and gently tumble the cannabis plant material during treatment. The rotation of the basket may be effected, for example, by means of rollers on which the basket is supported, or by means of a rotatable cage in which the basket is placed.

Another example of a microwave-vacuum dehydrator suitable for use as the pasteurizing unit and as the drying unit is a travelling wave-type apparatus, as shown in WO 2011/085467 (Durance et al.), commercially available from EnWave Corporation under the trademark quantaREV. The cannabis plant material is fed into the vacuum chamber and conveyed across a microwave-transparent window on a conveyor belt while being subjected to low pressure and microwave radiation. With this type of apparatus, the cannabis plant material is processed while resting on a tray or the conveyor belt, and is not subjected to tumbling.

EXAMPLES

Example 1

A sample of cannabis flower buds was pasteurized and then dried using a microwave vacuum apparatus of the batch-processing type, having a microwave-transparent basket rotatable about a horizontal axis to tumble the material. A 0.5 kg sample having an initial moisture content of 80 to 84 wt. % and at a temperature of 20° C. was loaded into the basket. The basket was placed in the vacuum chamber and rotated at 10 rpm. The vacuum chamber was evacuated to an absolute pressure of 180 Torr (240 mbar). Microwave power was applied at 1 kW for 5 minutes, at which point the cannabis flower bud temperature was 65° C. The vacuum chamber pressure was then reduced to 30 Torr (40 mbar) for a further 22 minutes, at 1 kW of microwave power. The dried sample was removed from the vacuum chamber. Its temperature was 48° C. and its moisture content was 11 wt. %. The product had a good structure. The operating parameters and test data are summarized in Table 1, below, for this and the following examples.

Example 2

A sample of cannabis flower buds was first dried and then pasteurized, using a microwave vacuum apparatus with rotary basket, of the type described in Example 1. A 0.5 kg sample having an initial moisture content of 80-84 wt. % and at a temperature of 20° C. was loaded into the basket. The basket was placed in the vacuum chamber and rotated at 10 rpm. The vacuum chamber was evacuated to an absolute pressure of 30 Torr (40 mbar). Microwave power was applied at 1 kW for 22 minutes. The vacuum chamber pressure was then increased to 180 Torr (240 mbar) for a further 5 minutes at 1 kW power. The dried sample was removed from the vacuum chamber. Its temperature was 54° C. and its moisture content was 12 wt. %. The operating parameters and test data are set out in Table 1. The reduction of TPC and final yeast and mold was less than in Example 1. The product had a satisfactory structure.

Example 3

A 0.5 kg sample of cannabis flower buds was first pasteurized and then dried using a microwave vacuum apparatus with rotary basket, of the type described in Example 1. The operating parameters and test data are set out in Table 1. The finished product had a compressed structure.

Example 4

A 4 kg sample of cannabis flower buds was first pasteurized and then dried using a microwave vacuum apparatus with rotary basket, of the type described in Example 1. The operating parameters and test data are set out in Table 1. The finished product had a satisfactory structure.

Example 5

A 4 kg sample of cannabis flower buds was first pasteurized and then dried, using a microwave vacuum apparatus with a rotatable rack holding eight trays. No covers were put over the trays. The rotation of the rack moved the trays (which remained horizontal) about the interior of the vacuum chamber during the pasteurization and drying process. A 4 kg sample having an initial moisture content of 80-84 wt. % and at a temperature of 20° C. was loaded onto the trays, at 0.5 kg per tray. The tray dimensions were 8.75 in. (21.9 cm)×27.25 (68 cm)×2.25 (5.6 cm) (L×W×H). The operating parameters and test data are set out in Table 1. The finished product had a satisfactory structure.

Example 6

A 4 kg sample of cannabis flower buds was first pasteurized and then dried, using a microwave vacuum apparatus with trays, of the type described in Example 5. The operating parameters and test data are set out in Table 1. The trays were covered with microwave transparent plastic covers, which were perforated sufficiently to allow steam to escape during the dehydration step but closed enough to retain enough steam to ensure a uniform cannabis temperature during the pasteurization step. The holes were approx. ½ inch in diameter and located every 2 inches across the width of the tray as well as along the tray length. The surface area of the holes was approximately 6.5 sq. inches (41.9 cm$^2$). The tray rack was placed in the vacuum chamber and rotated at 10 rpm. The vacuum chamber was evacuated to an absolute pressure of 300 Torr (400 mbar). Microwave power was applied at 5 kW for 10 minutes, at which point the product temperature was 75° C. The vacuum chamber pressure was then reduced to 30 Torr (40 mbar) for a further 27 minutes, at 5 kW of microwave power. The dried sample was removed from the vacuum chamber. Its temperature was 41° C. and its moisture content was 8 wt. %. The addition of plastic covers resulted in a greater reduction in Total Plate Count than was observed in Example 5 without plastic covers. The finished product had an excellent structure.

TABLE 1

|  | Example 1 | Example 2 | Example 3 | Example 4 | Example 5 | Example 6 |
|---|---|---|---|---|---|---|
| Microwave power (kW) | 1 | 1 | 1 | 5 | 5 | 5 |
| Rotation speed (rpm) | 10 | 10 | 10 | 10 | 10 | 10 |
| Pasteurization pressure (Torr) | 180 | 180 | 300 | 300 | 300 | 300 |
| Pasteurization time (min) | 5 | 5 | 3 | 10 | 10 | 10 |
| Pasteurization maximum temperature (° C.) | 65 | 65 | 75 | 75 | 75 | 75 |
| Drying pressure (Torr) | 30 | 30 | 30 | 30 | 30 | 30 |
| Drying time (min) | 22 | 22 | 22 | 27 | 27 | 27 |
| Drying maximum temperature (° C.) | 48 | 54 | 55 | 60 | 45 | 41 |
| Initial moisture (wt. %) | 80-84 | 80-84 | 80-84 | 80-84 | 80-84 | 80-84 |
| Final moisture (wt. %) | 11 | 12 | 8 | 14 | 8 | 8 |
| Initial TPC[1] (cfu/g) | 10,000 to 100,000 | 10,000 to 100,000 | 10,000 to 100,000 | 10,000 to 100,000 | 10,000 to 100,000 | 1,000,000 |
| Final TPC[1] (cfu/g) | 270 | 730 | <10 | <10 | <270 | $1.67 \times 10^3$ |
| Final yeast & mold (cfu/g) | 370 | 690 | 20 | <10 | <320 | N/A |
| Final BTGN[2] (cfu/g) | N/A | N/A | N/A | <10 | 10 to <100 | 10 to <100 [5] |
| Final terpene content (wt. %)[3] | 1.29 | 1.47 | 1.28 | N/A | N/A | N/A |
| Desired Cannabinoid (THC) retention (%)[4] | 100 | 100 | 100 | 100 | 100 | 100 |

[1]Total Plate Count.
[2]Bile Tolerant Gram Negative bacteria.
[3]The original terpene content was 1.5 to 2 wt. %.
[4]Percent of initial tetrahydrocannabinol that was retained in the dehydrated cannabis flower buds.
[5] The initial count was greater than $10^4$.

As will be apparent to those skilled in the art in the light of the foregoing disclosure, many alterations and modifications are possible in the practice of the teachings of the present disclosure without departing from the scope thereof. Accordingly, the scope of the present disclosure is to be construed in accordance with the following claims and the full range of allowable equivalents of the following claims.

The invention claimed is:

1. A method of pasteurizing and dehydrating cannabis plant material, comprising the steps of:
(a) loading the cannabis plant material into a vacuum chamber;
(b) reducing pressure inside the vacuum chamber to a first pressure less than atmospheric;
(c) maintaining the cannabis plant material in the vacuum chamber at the first pressure for a first time period at a pasteurizing temperature while irradiating the cannabis plant material with microwave radiation;
(d) reducing the pressure in the vacuum chamber after step (c) to a second pressure lower than the first pressure;
(e) maintaining the cannabis plant material in the vacuum chamber at the second pressure for a second time period at a dehydrating temperature lower than the pasteurizing temperature while irradiating the cannabis plant material with microwave radiation to dehydrate ft; and
(f) unloading the pasteurized and dehydrated cannabis plant material from the vacuum chamber.

2. A method of pasteurizing and dehydrating cannabis plant material, comprising the steps of:
(a) reducing pressure inside a first vacuum chamber to a first pressure less than atmospheric;
(b) loading the cannabis plant material into the first vacuum chamber;
(c) maintaining the cannabis plant material in the first vacuum chamber at the first pressure for a first time period at a pasteurizing temperature while irradiating the cannabis plant material with microwave radiation;
(d) unloading the pasteurized cannabis plant material from the first vacuum chamber;
(e) reducing pressure in a second vacuum chamber to a second pressure lower than the first pressure;
(f) loading the pasteurized cannabis plant material into the second vacuum chamber;
(g) maintaining the pasteurized cannabis pant material in the second vacuum chamber at the second pressure for a second time period at a dehydrating temperature lower than the pasteurizing temperature while irradiating the pasteurized cannabis plant material with microwave radiation to dehydrate it; and
(h) unloading the pasteurized and dehydrated cannabis pant material from the second vacuum chamber.

3. A method according to claim 2, wherein the first pressure is in the range of 150 to 400 Torr.

4. A method according to claim 2, wherein the first time period is in the range of 3 to 12 minutes.

5. A method according to claim 2, wherein the pasteurizing temperature is in the range of 60 to 95° C.

6. A method according to claim 2, wherein the second pressure is in the range of 10 to 60 Torr.

7. A method according to claim 2, wherein the second time period is in the range of 20 to 30 minutes.

8. A method according to claim 2, wherein the method reduces bacterial numbers to a total plate count≤50,000 cfu/g, total yeast and mold≤500 cfu/g, and BTGN<100 cfu/g.

9. A method according to claim 2, wherein the method reduces terpene content of the cannabis plant material by not more than 35%.

10. A method according to claim 2, wherein the method reduces desired cannabinoid content of the cannabis plant material by not more than 5%.

11. A method of dehydrating and pasteurizing cannabis plant material, comprising the steps of:
(a) loading the cannabis plant material into a vacuum chamber;
(b) reducing pressure inside the vacuum chamber to a first pressure less than atmospheric;
(c) maintaining the cannabis pant material in the vacuum chamber at the first pressure for a first time period at a dehydrating temperature while irradiating the cannabis plant material with microwave radiation to dehydrate it;
(d) increasing the pressure in the vacuum chamber after step (c) to a second pressure higher than the first pressure;
(e) maintaining the cannabis plant material in the vacuum chamber at the second pressure for a second time period at a pasteurizing temperature higher than the dehydrating temperature while irradiating the cannabis plant material with microwave radiation; and
(f) unloading the dehydrated and pasteurized cannabis plant material from the vacuum chamber.

12. A method of dehydrating and pasteurizing cannabis plant material, comprising the steps of:
(a) reducing pressure inside a first vacuum chamber to a first pressure less than atmospheric;
(b) loading the cannabis plant material into the first vacuum chamber;
(c) maintaining the cannabis plant material in the first vacuum chamber at the first pressure for a first time period at a dehydrating temperature while irradiating the cannabis plant material with microwave radiation to dehydrate it;
(d) unloading the dehydrated cannabis plant material from the first vacuum chamber;
(e) reducing pressure in a second vacuum chamber to a second pressure higher than the first pressure;
(f) loading the dehydrated cannabis plant material into the second vacuum chamber;
(g) maintaining the dehydrated cannabis plant material in the second vacuum chamber at the second pressure for a second time period at a pasteurizing temperature higher than the dehydrating temperature while irradiating the dehydrated cannabis plant material with microwave radiation; and
(h) unloading the dehydrated and pasteurized cannabis plant material from the second vacuum chamber.

13. A method according to claim 12, wherein the second pressure is in the range of 150 to 400 Torr.

14. A method according to claim 12, wherein the second time period is in the range of 3 to 12 minutes.

15. A method according to claim 12, wherein the pasteurizing temperature is in the range of 60 to 95° C.

16. A method according to claim 12, wherein the first pressure is in the range of 10 to 60 Torr.

17. A method according to claim 12, wherein the first time period is in the range of 20 to 30 minutes.

18. A method according to claim 12, wherein the method reduces terpene content of the cannabis plant material by not more than 35%.

19. A method according to claim 12, wherein the method reduces desired cannabinoid content of the cannabis plant material by not more than 5%.

* * * * *